US006190681B1

(12) United States Patent
Fishman

(10) Patent No.: US 6,190,681 B1
(45) Date of Patent: Feb. 20, 2001

(54) LONG LASTING LIQUID COLOR COMPOSITIONS

(76) Inventor: Yoram Fishman, 3300 Wonderview Plz., Los Angeles, CA (US) 90068

( * ) Notice: Under 35 U.S.C. 154(b), the term of this patent shall be extended for 0 days.

(21) Appl. No.: 09/294,712

(22) Filed: Apr. 15, 1999

Related U.S. Application Data

(63) Continuation-in-part of application No. 09/060,799, filed on Apr. 15, 1998.

(51) Int. Cl.[7] .......................... A61K 7/021; A61K 7/025
(52) U.S. Cl. ............................. 424/401; 424/63; 424/64
(58) Field of Search ......................... 424/64, 401, 63

(56) References Cited

U.S. PATENT DOCUMENTS

| | | | |
|---|---|---|---|
| 2,230,063 | 1/1941 | Klimist | 167/85 |
| 2,566,722 | 9/1951 | Friedberg | 91/54.7 |
| 3,646,214 | 2/1972 | Katz | 424/362 |
| 3,927,199 | 12/1975 | Micchelli et al. | 424/47 |
| 4,192,861 | 3/1980 | Micchelli et al. | 424/47 |
| 4,315,910 | 2/1982 | Nowak, Jr. et al. | 424/47 |
| 4,534,961 | 8/1985 | Liff | 424/63 |
| 4,795,631 | 1/1989 | Sheehan | 424/64 |
| 4,873,078 | 10/1989 | Edmundson et al. | 424/64 |
| 4,904,698 | 2/1990 | Adkins, Jr. et al. | 514/642 |
| 4,935,228 | 6/1990 | Finkenaur et al. | 424/64 |
| 4,978,524 | 12/1990 | Kamen et al. | 424/64 |
| 4,980,167 | 12/1990 | Harashima et al. | 424/401 |
| 4,996,044 | 2/1991 | Mercado et al. | 424/64 |
| 5,085,855 | 2/1992 | Shore | 424/64 |
| 5,085,856 | 2/1992 | Dunphy et al. | 424/64 |
| 5,093,111 | 3/1992 | Baker et al. | 424/64 |
| 5,106,609 | 4/1992 | Bolich, Jr. et al. | 424/70 |
| 5,108,736 | 4/1992 | Schlossman | 424/64 |
| 5,143,723 | 9/1992 | Calvo et al. | 424/63 |
| 5,200,172 | 4/1993 | Kamen et al. | 424/64 |
| 5,238,678 | 8/1993 | Shiozawa et al. | 424/64 |
| 5,288,493 | 2/1994 | Martino et al. | 424/401 |
| 5,505,937 | 4/1996 | Castrogiovanni et al. | 424/64 |
| 5,648,066 | 7/1997 | Stepniewski | 424/64 |
| 5,653,970 | 8/1997 | Vermeer | 424/70.24 |
| 5,665,364 | 9/1997 | McAtee et al. | 424/401 |
| 5,667,770 | 9/1997 | Szweda et al. | 424/64 |
| 5,690,918 | 11/1997 | Jacks et al. | 424/64 |
| 5,747,017 | 5/1998 | Nichols et al. | 424/61 |
| 6,001,374 | 12/1999 | Nichols | 424/401 |
| 6,010,709 | 1/2000 | Nichols | 424/401 |

FOREIGN PATENT DOCUMENTS

| | | |
|---|---|---|
| 0005922 | 12/1979 | (EP) . |
| 2638636 | 11/1988 | (FR) . |
| WO86/02001 | 4/1986 | (WO) . |
| WO92/19215 | 11/1992 | (WO) . |

OTHER PUBLICATIONS

"Harry's Cosmeticology", pp. 332–333 (Colored Make–up Preparations), 7th Ed., Chemical Publishing Co. 1982.
Amphomer brochure by National Starch and Chemical Company.
Aqualon catalog for Klucel® Hydroxyproplcellulose, Feb. 1991.
Americhol® catalog for Methyl Glucoside Products, Jun. 1995.
Sphereon Functional Microbeads catalog, Sep. 1997.
Personal Care Polymers catalog from National Starch and Chemical Co., 1996.
Lip Ink International Product Information pages, 1997.

*Primary Examiner*—Thurman K. Page
*Assistant Examiner*—S. Howard
(74) *Attorney, Agent, or Firm*—Konrad, Raynes & Victor, LLP; Alan S. Raynes

(57) ABSTRACT

Embodiments include a liquid colorant composition having an acrylates/octylacrylamide copolymer, a cellulose material, alcohol and a colorant. The cellulose material may be hydroxypropylcellulose. Isostearyl alcohol and silica may be included in the composition to enhance properties such as the spreadability and feel of the composition on the lips. Additional additives such as fragrance and botanical extracts may also be added. Such compositions can be easily applied to the lips and offer long wear characteristics.

20 Claims, 2 Drawing Sheets

LONG LASTING LIQUID COLOR COMPOSITIONS

This is a continuation-in-part of application Ser. No. 09/060,799, filed Apr. 15, 1998.

FIELD OF THE INVENTION

Embodiments of the present invention relate to long-lasting liquid color formulations for application to the skin and methods for manufacturing such formulations.

DESCRIPTION OF THE RELATED ART

Colorant materials have been used for many years to highlight the lips and other skin regions on the body. Most conventional lipstick formulations have a semisolid consistency, and include a colorant such as a pigment mixed with an oily vehicle such as a fat or oil stiffened to a desired consistency with one or more waxes. In recent years, attempts have been made to provide a lipstick having a long lasting color, in order to lessen the need for frequent reapplication and to avoid problems such as the lipstick rubbing off of the lips and onto clothing.

One type of lipstick formulation increases the concentration of the colorant in an effort to obtain long lasting color. However, increasing the concentration of the colorant can cause the lipstick to become too dry on the lips. Moisturizers and conditioning agents can be added to the formulations, but these components are not durable and can adversely affect the appearance of the lipstick on the lips.

Another type of lipstick formulation includes a ceramide component. Ceramides are a group of lipids, members of which are found in the epidermis of mammals. Chemically, ceramides are N-acrylated sphingosine bases. Ceramide lipstick formulations also typically contain hydrocarbon waxes. Such formulations may provide some improvement, but even longer wear lipstick formulations are desirable.

Colorants used for application to skin other than the lips, such as tattoos on the arms, may be injected into the skin in order to form a permanent tattoo. Other colorant formulations (like magic marker ink) may be used to stain the skin for a relatively short time period, for example, a few hours. It would be desirable to be able to color the skin for a longer time period, while at the same time not permanently staining the skin.

SUMMARY

Embodiments of the present invention provide a liquid lipstick including effective amounts of a copolymer having an acrylate/methacrylate component, an N-substituted acrylamide component, and an unsaturated carboxylic acid component. The liquid lipstick also includes a cellulose material, and at least one alcohol. The cellulose material may be hydroxypropylcellulose. One or more colorant materials may be included in the composition, and other additives may be added to enhance properties such as the feel of the composition on the lips. Additional additives such as fragrance and botanical extracts may also be added. Such compositions can be easily applied to the lips and offer long wear characteristics.

Other embodiments include a liquid colorant composition for coloring skin. The composition includes an acrylates/octylacrylamide copolymer consisting essentially of 10–75% by weight acrylate/methacrylate, 10–70% by weight N-substituted acrylamide and 5–40% by weight unsaturated carboxylic acid. The composition also includes a thickener material, alcohol and colorant.

Another embodiment relates to a liquid composition for coloring skin including effective amounts of an acrylates/octylacrylamide copolymer having an acrylate/methacrylate component, an N-substituted acrylamide component and an unsaturated carboxylic acid component. The embodiment also includes hydroxypropylcelluose as a thickener. Additional ingredients include isostearyl alcohol, ethanol, and colorant.

BRIEF DESCRIPTION OF THE DRAWINGS

Embodiments of the invention are described with reference to the accompanying drawing which, for illustrative purposes, is schematic and not drawn to scale.

DESCRIPTION OF PREFERRED EMBODIMENTS

Figure 1:
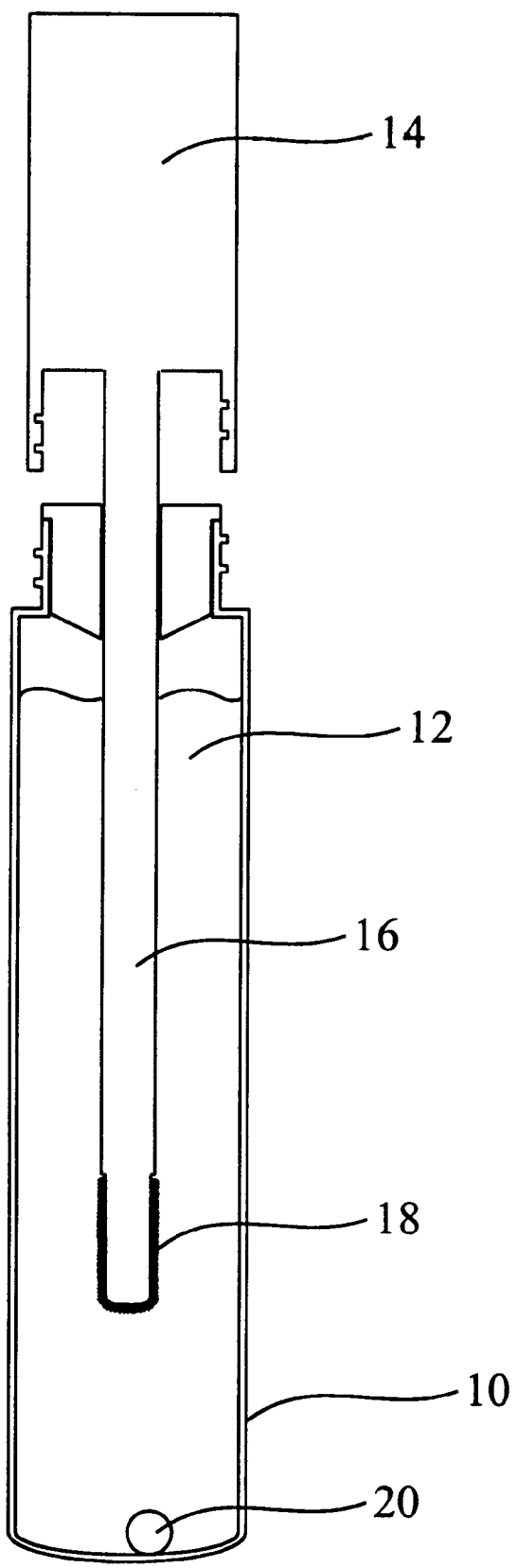
FIG. 1 illustrates a cross-sectional view of a container which may be used for storing and applying lipstick compositions formed according to embodiments of the present invention.

Embodiments of the present invention relate to skin coloring formulations having long life and easy application. Certain preferred embodiments include liquid lipstick compositions containing an acrylates/octylacrylamide copolymer (CTFA designation) component, a thickener component and an alcohol component. It is believed that the acrylates/octylacrylamide copolymer acts to bind the colorant to the skin, yielding a long-lasting lipstick. Certain preferred embodiments utilize an anionic acrylates/octylacrylamide copolymer powder available under the trade name Dermacryl® 79 acrylates/octylacrylamide copolymer, sold by National Starch & Chemical Company (Bridgewater, N.J.). Dermacryl® 79 is a hydrophobic, high molecular weight carboxylated acrylic copolymer. Another acrylates/octylacrylamide copolymer is available under the trade name Dermacryl® LT (National Starch & Chemical Company). Preferred embodiments may include approximately 0.5 to approximately 10 weight percent of copolymer, preferably the Dermacryl® 79 acrylates/octylacrylamide copolymer, in the composition, with certain more preferred embodiments including approximately 3.5 to 4.5 weight percent.

Preferred copolymers for use in certain embodiments are described in U.S. Pat. No. 5,288,493, which is hereby incorporated by reference in its entirety. Certain preferred copolymers involve three components: a) an acrylate/methacrylate, b) an N-substituted acrylamide and c) an unsaturated carboxylic acid. More particularly, the copolymers comprise a) from about 10–75% by weight of $C_1$ to $C_{18}$, preferably $C_3$ to $C_8$ alkyl acrylate/methacrylate; b) from about 10 to 70% by weight of $C_1$ to $C_{18}$, preferably $C_4$ to $C_{10}$ N-substituted alkyl acrylamide and c) from about 5 to 40% by weight of unsaturated carboxylic acid of 3 to 5 carbon atoms, preferably acrylic or methacrylic acid, wherein the percentages total 100%. Preferably, these copolymers comprise 30 to 60% by weight of the acrylate/methacrylate, 15 to 60% by weight of the acrylamide and 10 to 25% by weight of the carboxylic acid. More preferably the acrylamide will comprise 20 to 40% by weight of the copolymer and even more preferably 25 to 35% by weight.

Several examples of acrylate/methacrylates include isobutyl methacrylate, butyl acrylate, and methyl methacrylate. An example of an N-substituted acrylamide is t-octylacrylamide. Some examples of copolymer formulations include: (1) 65% isobutyl methacrylate, 10% t-octylacrylamide, and 25% acrylic acid; (2) 15% isobutyl methacrylate, 60% t-octylacrylamide, and 25% acrylic acid; (3) 40% isobutyl methacrylate, 30% t-octylacrylamide, and 30% acrylic acid; (4) 10% butyl acrylate, 35% methyl methacrylate, 30% t-octylacrylamide, and 25% acrylic acid; (5) 45% isobutyl methacrylate, 30% t-butylacrylamide, and 25% acrylic acid; (6) 35% isobutyl methacrylate, 30% t-octylacrylamide, and 35% acrylic acid; (7) 25% isobutyl methacrylate, 70% t-octylacrylamide, and 5% acrylic acid; and (8) 51% isobutyl methacrylate, 30% N substituted t-octylacrylamide, and 19% acrylic acid.

An example of a method for forming an acrylate/methacrylate, acrylamide, acid copolymer having the components specified in example (8) in the preceding paragraph is as follows: A reaction vessel equipped with a condenser and mechanical agitation means may be charged with 51 parts of isobutyl methacrylate, 30 parts of N-substituted t-octylacrylamide, 19 parts of acrylic acid, 2.0 parts of free radical initiator and 100 parts of ethanol. The contents may be heated to the reflux temperature of the system and held there for a period of six hours, whereupon an additional 1.0 part of the initiator may be added thereto. The system may then be held at reflux for an additional four hours and then the reaction then cooled to 30° C. and the polymer recovered by standard separation means.

Numerous thickener components may be utilized in embodiments of the present invention, such as, for example, cellulose gums. A preferred cellulose thickener is a hydroxypropylcellulose powder, available under the trade name Klucel™, type 99-HFF, sold by Aqualon Company (Wilmington, Del.). Preferred embodiments may include approximately 0.1 to approximately 5.0 weight percent thickener, with certain more preferred embodiments including approximately 0.1 to approximately 1.0 weight percent. It is believed that the thickener component also acts to inhibit color bleeding.

Numerous dyes and pigments or color enhancing components may be utilized in lipstick compositions according to embodiments of the present invention including, for example, U.S. Government certified colors, both Drug and Cosmetic grade and Food, Drug and Cosmetic grade. Typical colorant materials might include various lakes, iron oxides, micas, and titanium dioxides. Some specific examples are sold under the following trade names or designations: Permashade WP10S (Persperce Inc. of NJ); Flamenco Super Orange 330Z, Flamenco Super Violet 530Z, Flamenco Gold 220C (Mearl Corp., Ossining, N.Y.); D&C Red #28 Aluminum Lake or C14-6623, D&C Red #33 Aluminum Lake or C17-7744, D&C Red #7 or C19-031, Black Iron Oxide or C33-7734, Russet Iron Oxide or C33-7775, FD&C Yellow #5 Aluminum Lake or C69-7724, D&C Orange #5 or C14-033, (Sun Chemical Corp., Staten Island, N.Y.); Cosmetic Brown Dark Iron Oxide or CG-975, Cosmetic Red Iron Oxide or CG-140, Cosmetic Red Iron Oxide or CG-180, Ultramarine or CG-225, (Whittaker, Clark & Daniels, South Plainfield, N.J.); Chromolite Mauve and Chromolite Red (from ISP-Van Dyk, Wayne, N.J.); Colorona Bordeaux 017405, Colorona Copper Fine 017385, (Rona/EM Industries, Hawthorne, N.Y.); Timiron MP24 Karat Gold (Rona/EM Industries, Hawthorne, N.Y.). Numerous other colorants may also be used. Often more than one component is used to form the desired lipstick colorant and the total amount of colorant may in certain embodiments range up to approximately 10 weight percent, with preferred lipstick embodiments having up to approximately 4 weight percent.

Depending on its texture, the colorant may be mixed with a liquid to form a slurry and then milled to break up the particles of pigment and obtain a product having better spreadability. Some examples of liquids which may be mixed with the colorant prior to milling include an oil such as castor oil, glycerine, or propylene glycol. A preferred liquid for mixing with the colorant is sold as Glucam P-20 or PPG-20 Methyl Glucose Ether, by Americhol Corporation (Edison, N.J.). In some embodiments approximately 2 parts of the PPG-20 Methyl Glucose Ether is mixed with 1 part colorant, although a variety of mixtures such as 1 to 1 and others are possible as long as a slurry is created. Certain embodiments may include up to approximately 5 weight percent methyl glucose ether, with more preferred embodiments including approximately 0.5 to approximately 4.5 weight percent. Generally lakes, iron oxides, and titanium dioxides are milled. It is generally not necessary to mill alcohol soluble pigments, alcohol soluble lakes, and micas. A variety of mills, including a three roller mill manufactured by Exakt (OK), may be utilized.

In certain embodiments, the colorant is mixed with a component to improve its spreadability characteristics. This component may be a fatty alcohol such as, for example, isostearyl alcohol sold under the trade name Witcohol 66, sold by Witco Chemical Company (CT), or Prisorino 3515, sold by Unichem International. Certain embodiments may include up to approximately 20 weight percent isostearyl alcohol, with preferred embodiments including up to approximately 5 weight percent and even more preferred embodiments including approximately 2 to approximately 4 weight percent. In other embodiments it may be possible to use fatty acids such as isostearyl acid to improve the spreadability of the colorant.

Embodiments may also include an additional ingredient for improving the feel of the lipstick on the lips. Preferred embodiments utilize fine silica particles, which are mixed with the colorant after milling. It is also believed that the silica component contributes to the adhesion of the lipstick to the lips. Such a silica is sold under the trade name Spheron™ 1500, by Presperse Inc. (NJ). Certain embodiments may include up to approximately 10 weight percent silica, with preferred embodiments including approximately 1 to approximately 2 weight percent. Fine particles of other materials, such as, for example, boron nitride, may also be used in other embodiments to improve the feel of the lipstick on the lips.

Additional ingredients may also be added to embodiments of the present invention for masking the effects of alcohol present in the lipstick composition. Preferred ingredients include fragrances and botanical extracts. The fragrance acts to mask the smell of the alcohol and the extracts can inhibit stinging on the lips due to the alcohol. One such preferred liquid fragrance is sold under the name Botanical Naturalizer #6633, by Belle Aire Fragrances (IL). Certain embodiments may include up to approximately 10 weight percent liquid fragrance, with preferred embodiments including approximately 1 to approximately 1.5 weight percent. A preferred botanical extract is sold under the name Phytodesensitizer, by Ichimaru Pharcos Co., Ltd., (Japan). Certain embodiments may include up to approximately 10 weight percent botanical extract, with preferred embodiments including approximately 0.5 to approximately 1.5 weight percent.

Embodiments of the present invention also relate to methods for forming liquid lipstick compositions. One method for manufacturing embodiments of the present invention is as follows. In a first container, the hydroxypropylcellulose powder (trade name Klucel) is combined with an alcohol, preferably ethyl alcohol (for ex., SD Alcohol 40 sold by Remet, Shell Chemical, etc.) in an amount of approximately 2 parts powder to 98 parts alcohol. The contents are covered and preferably mixed for a time of up to 2.5 hours to form a first solution that is somewhat clear and has a relatively thick consistency. Depending on the quantities of the components being mixed, the equipment used, and other variables, the appropriate mixing times may vary considerably. In a second container, the acrylates/octylacrylamide copolymer powder (trade name Dermacryl® 79) is combined with an alcohol, preferably ethyl alcohol, in an amount of approximately 10 parts powder to 90 parts alcohol. The contents may be covered and preferably mixed for a time of up to about 30 minutes to form a second solution that is more clear than the first solution and has a less viscous consistency.

The colorant to be mixed with the first and second solutions may be formed by mixing one or more pigments with methyl glucose ether (trade name Glucom P-20 or PPG-20) to form a slurry and then milling the slurry (if necessary). For bulk quantities of components the milling may, for example, be carried out for about 5 minutes per pound of slurry. The slurry may then optionally be mixed with any other coloring components that do not require milling such as, for example, mica. The mica may act as a color enhancer and provides good iridescence. Other optional components may include isostearyl alcohol, which gives the lipstick good spreadability on the lips, and silica particles, which give the lipstick improved feel and adhesion on the lips. These components are combined with ethanol and mixed until a uniform colorant composition is obtained.

Next the colorant composition, the first solution and the second solution are combined and mixed to form a uniform and semi-viscous liquid. In certain embodiments the colorant composition is first mixed with the first solution and then the mixture of the colorant and first solution is mixed with the second solution. If any alcohol has been lost (for example, evaporated) from the mixture, a quantity sufficient may be added when the solutions are mixed together. Additional ingredients may be optionally added at this time to mask the effects of the alcohol in the composition. Preferably these ingredients include a fragrance such as Botanical Naturalizer (sold by Belle Aire Fragrances) to mask the smell of the alcohol and botanical extracts such as Phyto-desensitizer (sold by Ichimaru Pharcos Co., Ltd., Japan) to inhibit stinging on the lips from the alcohol. The components are mixed until a substantially uniform liquid lipstick mixture is obtained. The lipstick mixture may then be packaged, for example, in a tubular bottle having an applicator (or wand) with a tip brush or pad to apply the liquid lipstick to the lips. One example of a container and applicator is illustrated in FIG. 1, which is a cross-sectional view of a vial 10 containing a liquid lipstick 12 according to embodiments of the present invention. Also included is a cap 14 having an integrated wand 16 and tip 18 for applying the liquid lipstick 12 to the lips. The container and applicator illustrated in FIG. 1 are sold under the product name Mini Lip Gloss Container by World Wide Packaging (East Hanover, N.Y.). One or more small balls 20 may also be provided in the vial 10 for mixing the lipstick 12. Other types of containers and applicators such as, for example, a roller, could also be used.

Examples of liquid lipstick compositions for achieving various colors according to certain embodiments of the present invention are set forth in Tables I and II below. Since there may be many modifications with departing from the scope of the invention, the examples below are not intended to limit the invention but to illustrate certain aspects of the invention more clearly.

TABLE 1

Example of composition for red liquid lipstick color.

| Ingredient | Red |
| --- | --- |
| Isostearyl Alcohol | 3.20 |
| Silica | 1.50 |
| Ethanol (SD Alcohol 40) | 81.37 |
| Hydroxypropylcellulose | 0.50 |
| Acrylates/Octylacrylamide Copolymer | 4.50 |
| PPG-20 Methyl Glucose Ether | 4.10 |
| Phyto Desensitizer (Botanical Extract Mixture) | 1.00 |
| Fragrance (Naturalizer #6633) | 1.20 |
| Permashade WP10S | 0.60 |
| Iron Oxides CG 140 | 0.82 |
| DC Red #28 Aluminum Lake C14-6623 | 0.30 |
| DC Red #33 Aluminum Lake C17-7744 | 0.07 |
| DC Yellow #5 Aluminum Lake C69-7724 | 0.21 |
| DC Red #7 C19–031 | 0.63 |

TABLE 2

Examples of compositions for light bronze, dusty rose and blush liquid lipstick colors.

| Ingredient | Light Bronze | Dusty Rose | Blush |
| --- | --- | --- | --- |
| Isostearyl Alcohol | 3.20 (wt %) | 3.20 (wt %) | 3.20 (wt %) |
| Silica | 1.50 | 1.50 | 1.50 |
| SD Alcohol 40 | 84.04 | 85.30 | 84.05 |
| Hydroxypropylcellulose | 0.50 | 0.50 | 0.50 |
| Acrylates/Octylacrylamide Copolymer | 4.50 | 4.50 | 4.50 |
| Methyl Glucose Ether | 1.19 | 0.525 | 1.50 |
| Permashade WP10S | — | — | 0.90 |
| Iron Oxide | 0.55 | — | — |
| D&C Orange #5 | 0.10 | 0.10 | 0.10 |
| D & C Red #33 Aluminum Lake | 0.07 | 0.20 | 0.05 |
| Black Iron Oxide | 0.50 | 0.125 | — |
| Flamenco Super Orange 330z | 0.50 | — | — |
| Timeron MP 24 Karat Gold | 1.15 | — | — |
| Cosmetic Brown Dark Iron Oxide | — | — | 0.50 |
| Chromolite Mauve | — | 1.85 | 1.00 |
| Phyto Desensitizer | 1.00 | 1.00 | 1.00 |
| Fragrance | 1.20 | 1.20 | 1.20 |

TABLE 3

Examples of compositions for sheer pink, dark pink, and nude liquid lipstick colors.

| Ingredient | Sheer Pink | Dark Pink | Nude |
| --- | --- | --- | --- |
| Isostearyl Alcohol | 3.20 (wt %) | 3.20 (wt %) | 3.20 (wt %) |
| Silica | 1.50 | 1.50 | 1.50 |
| SD Alcohol 40 | 82.95 | 82.71 | 85.80 |
| Hydroxypropylcellulose | 0.50 | 0.50 | 0.50 |
| Acrylates/Octylacrylamide Copolymer | 4.50 | 4.50 | 4.50 |
| Methyl Glucose Ether | 1.45 | 2.56 | 0.85 |
| Permashade WP10S | 0.70 | — | 0.50 |
| D&C Red #33 Aluminum Lake | — | 0.17 | — |
| D&C Red #28 Aluminum Lake | 0.45 | 0.55 | — |

TABLE 3-continued

Examples of compositions for sheer pink, dark pink, and nude liquid lipstick colors.

| Ingredient | Sheer Pink | Dark Pink | Nude |
| --- | --- | --- | --- |
| Ultra Marine Pink | — | 1.25 | — |
| Russet Iron Oxide | 0.75 | — | — |
| Cosmetic Red Iron Oxide | — | 0.75 | — |
| FD&C Yellow #5 Aluminum Lake | — | 0.11 | — |
| Cosmetic Brown Dark Iron Oxide | — | — | 0.35 |
| Flamenco Super Orange 330z | 0.80 | — | — |
| Colorona Bordeaux | 1.00 | — | — |
| Chromolite Mauve | — | — | 0.60 |
| Phyto Desensitizer | 1.00 | 1.00 | 1.00 |
| Fragrance | 1.20 | 1.20 | 1.20 |

Depending on the lipstick appearance desired by the user, a separate gloss component may be applied over the lipstick on the lips in order to enhance the shine and texture of the lipstick on the lips. The gloss composition may be applied after the lipstick has been placed on the lips. The gloss may include a number of water insoluble silicones and other components for enhancing the appearance of the lips such as vitamins. A preferred gloss composition includes a dimethicone component, a trimethyl silylamodimethicone and octoxynol-40 component (sold as Dow Corning Q2 7224), and vitamins such as tocopherol (sold by Henkel), panthenol (sold by Roche Chemicals) and retinyl palmitate (sold by Roche Chemicals). The dimethicone may include a variety of silicones. One preferred dimethicone mixture contains three silicones sold under the following names: (1) Dow Corning 200 Fluid (sold by Dow Corning), (2) GE Viscasil 60M (sold by General Electric), and (3) GE SF96-1000 (sold by General Electric). These components may preferably be heated to a temperature of approximately 55–60° C. and then mixed together. An example of a preferred gloss composition is set forth in Table 4. It is believed that other silicones and resins may also be used. However, the components selected should not remove the color from the lips or otherwise adversely react with the lipstick formulation. The gloss may also be packaged in a variety of containers such as, for example, a container similar to that illustrated in FIG. 1.

TABLE 4

Lip Gloss Composition

| Component | Weight Percent |
| --- | --- |
| Dow Corning 200 Fluid (Dimethicone) | 49.35 |
| GE Viscasil 60M (Dimethicone) | 45.00 |
| GE SF96-1000 (Dimethicone) | 4.50 |
| Trimethyl Amodimethocone and Octoxynol-40 | 0.75 |
| Tocopherol | 0.10 |
| Panthenol | 0.20 |
| Retinyl Palmitate | 0.10 |

Depending on the color and desired thickness, the lipstick may be applied as one or several layers. If applied in several layers it is preferable to let each layer dry prior to applying the next layer. After the lipstick dries, the gloss may be applied if desired.

Liquid lipsticks and gloss according to embodiments of the present invention were compared against conventional semisolid lipsticks in a number of tests. In the first test, the conventional lipstick and the liquid lipstick and gloss according to an embodiment of the present invention were applied to a person's lips. The lips were then dabbed with a napkin 15 times and the amount of color lost from the lips was evaluated. The conventional lipstick lost about 70% of its color, whereas the liquid lipstick and gloss had no apparent loss of color. In the second test, after application to the lips the test subjects ate a regular meal. The amount of color remaining on the lips after the meal was evaluated, with the conventional lipstick losing about 90% of its color and the liquid lipstick and gloss losing about 10% of its color. In the third test, after application the test subjects went to bed overnight and the amount of color remaining on the lips the next morning was evaluated. The conventional lipstick lost about 70% of its color and the liquid lipstick and gloss lost about 10% of its color.

It is possible to remove the lipstick formulations from the lips using a mixture of components. The preferred components include a homopolymer of dimethylaminoethyl methasynylate such as that sold under the name Salcare SC 96 by Allied Colloids (Suffolk, Va.). The Salcare SC 96 contains a number of ingredients including polyquarternium-37, propylene glycol dicaprylate/dicaprate, and PPG-1 trideceth-6. Other additives may include fragrance, tocopherol and panthenol. Preferably the lipstick remover contains the above components mixed with ethanol in approximately the amounts listed in Table 5. It may also be possible to remove the lipstick using other formulations including, for example, water soluble silicones. The remover may also be packaged in a variety of containers, such as, for example, that illustrated in FIG. 1. Various combinations of lipstick, gloss and lipstick remover may be packaged together and sold as a kit.

TABLE 5

Lipstick Remover

| Ingredient | Weight Percent |
| --- | --- |
| SD Alcohol 40 | 94.00 |
| Polyquarternium-37 and Propylene Glycol Dicaprylate/Dicaprate | 3.80 |
| Fragrance (Naturalizer #6633) | 2.00 |
| Tocopherol | 0.10 |
| Panthenol | 0.10 |

Another aspect of embodiments of the present invention relates to formulations for applying long-lasting but not permanent color to skin on the body other than the lips. The lips may be more sensitive than other skin regions, and therefore certain ingredients and their concentrations may differ between lipstick and other skin embodiments. For example, tattoo embodiments may employ a higher percentage of colorant than lipstick formulations. Certain embodiments include an acrylates/octylacrylamide copolymer component and a thickener component (for example, a cellulose material such as hydroxypropylcellulose). Examples of several preferred temporary tattoo compositions are set forth in Table 6.

TABLE 6

Examples of temporary tattoo compositions.

| Ingredient | Red A | | Red B |
| --- | --- | --- | --- |
| Ethanol (SD Alcohol 40) | 75.60 | (wt %) | 89.80 |
| Isostearyl Alcohol | 2.00 | | 1.70 |
| Acrylates/Octylacrylamide Copolymer | 4.00 | | 4.00 |
| Methyl Glucose Ether | 2.00 | | 2.67 |
| D&C Red #28 Aluminum Lake | — | | 0.30 |
| D&C Red #7(C19–031) | 1.00 | | 1.33 |
| Hydroxypropylcellulose | 0.40 | | 0.20 |
| Isopropyl Alcohol | 12.00 | | — |
| Shellac | 3.00 | | — |

Embodiments of the present invention also relate to methods for manufacturing skin tattoo compositions. Preferred tattoo embodiments are made up of a liquid composition that can be applied to skin and which is temporary in nature. By temporary it is meant that the tattoo is not permanent in the sense of traditional tattoos in which a needle is inserted into through the skin and a colorant injected to form a permanent image. In certain embodiments the components are mixed with alcohol and combined with colorants in a manner similar to that described above for the lipstick compositions.

One example of a manufacturing method for forming a tattoo composition is as follows. Isopropyl alcohol and shellac are combined and mixed in a mixing tank until the solution is complete. Isostearyl alcohol is added and the solution is mixed until uniform. The colorant (for example, DC Red #7) may be mixed with methyl glucose ester to form a slurry and then the slurry is milled. A solution is formed of hydroxypropylcellulose (Klucel HFF) and ethanol (for example, about 2% Klucel HFF to 98% ethanol may be used) and mixed until the hydroxypropylcellulose is dissolved. The hydroxypropylcellulose solution is combined with the milled colorant and mixed. A separate solution is formed by mixing the acrylates/octylacrylamide copolymer (Dermacryl 79) and ethanol (for example, about 10% Dermacryl 79 to 90% ethanol) until the acrylates/octylacrylamide copolymer is dissolved. The acrylates/octylacrylamide copolymer solution is then combined with the other components. A quantity sufficient of ethanol may be added (if necessary) and the components are mixed until uniform.

Due to differences between the lips and the skin that a tattoo is applied to (such as, for example, the arm), certain components included in embodiments of the liquid lipstick may or may not be necessary in the tattoo formulation and ingredients common to both may have differing compositions. Certain preferred tattoo embodiments include approximately 0.5 to approximately 10 weight percent acrylates/octylacrylamide copolymer, with more preferred embodiments including approximately 3.5 to 4.5 weight percent. It is believed that the acrylates/octylacrylamide copolymer acts to bind the colorant to the skin. Certain tattoo embodiments also include approximately 0.1 to approximately 5 weight percent hydroxypropylcellulose to act as a thickener, with more preferred embodiments including approximately 0.1 to approximately 1.0 weight percent. Certain embodiments also include up to approximately 10 weight percent colorant. Embodiments may also include a liquid mixed with the colorant to form a slurry prior to milling. One such liquid is methyl glucose ether. Certain embodiments include up to approximately 5 weight percent methyl glucose ether, with more preferred embodiments including approximately 2 to approximately 3 weight percent. Embodiments may also include one or more component to improve spreadability on the skin. One such component is isostearyl alcohol. Certain embodiments include up to approximately 20 weight percent isostearyl alcohol, with certain more preferred embodiments including approximately 1 to approximately 3 weight percent isostearyl alcohol. Certain embodiments may also include isopropyl alcohol (preferably up to approximately 20 weight percent) and shellac (preferably up to approximately 10 weight percent) in order to further improve color spreadability and improve shine. In addition, the lips are generally more sensitive and are subject to more frequent contact with saliva and other liquids than other body regions such as, for example, the arms, legs and torso. Thus, certain ingredients such as the Phyto Desensitizer and Fragrance that are used in some liquid lipstick embodiments are not necessary in certain tattoo embodiments. It may also be possible to use a larger quantity of the acrylates/octylacrylamide copolymer in certain tattoo embodiments than the quantity used in certain lipstick embodiments.

Figure 2:
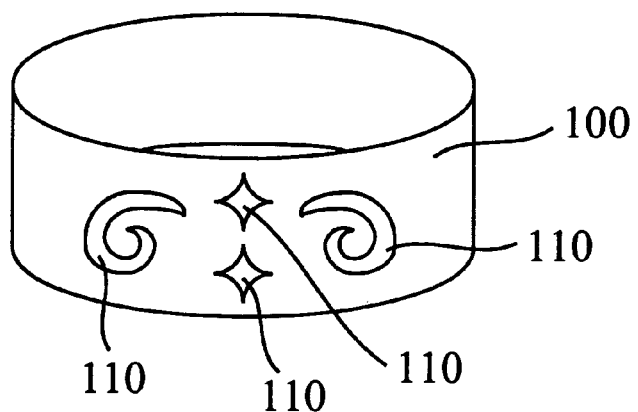
FIG. 2 illustrates a view of a band having a cut out design for use as a stencil according to embodiments of the present invention.

The tattoo formulations may be applied to the skin using a variety of applicators. One preferred applicator is a spray bottle or can. Alternatively a roll-on applicator or a wand applicator (such as that illustrated in FIG. 1) could be used. A stencil may be utilized together with the liquid tattoo formulation. The stencil may be placed on the appropriate location on the skin, and the liquid tattoo formulation applied over the stencil. One example of a stencil includes a cut out design and a temporary adhesive for sticking the stencil on the skin. Another stencil may include, for example, a band that has a cut out design incorporated therein, such as the band 100 illustrated in FIG. 2, which includes cut out regions 110 through which the liquid tattoo formulation will be applied. If desired the cut out regions 110 may extend around the entire band 100. The band 100 may fit over or around a portion of the body such as, for example, an arm or leg. The band may be elastic or may have some other attachment mechanism (clip, velcro, etc.) for fitting around any portion of the body.

Test results have indicated that tattoo mixtures such as those set forth in Table 6 will last on the skin for approximately 3 days on the skin under normal wear. The tattoo formulation may be quickly removed from the skin using a remover such as that described above for removing lipstick formulations. Various combinations of the components (for example, stencil, tattoo formulation, remover) may be packaged together as a kit.

It will, of course, be understood that modifications of the present invention, in its various aspects, will be apparent to those skilled in the art. Other embodiments for coloring the skin are also possible, their specific features depending upon the particular application. Therefore, the scope of the invention should not be limited by the particular embodiments herein described but should be defined by the appended claims and equivalents thereof.

What is claimed:

1. A liquid lipstick comprising effective amounts of:
    a copolymer consisting essentially of:
        an acrylate/methacrylate component;
        an N-substituted acrylamide component; and
        an unsaturated carboxylic acid component;
    a cellulose material;
    at least one alcohol; and
    a colorant.
2. A liquid lipstick as in claim 1, said copolymer consisting essentially of:

10–75% by weight of $C_1$ to $C_{18}$ alkyl acrylate/methacrylate;

10–70% by weight of $C_1$ to $C_{18}$ N-substituted alkyl acrylamide; and 5 to 40% by weight of unsaturated carboxylic acid of 3 to 5 carbon atoms.

3. A liquid lipstick as in claim 1, said copolymer consisting essentially of:

30–60% by weight of $C_1$ to $C_{18}$ alkyl acrylate/methacrylate;

15–60% by weight of $C_1$ to $C_{18}$ N-substituted alkyl acrylamide; and

10–25% by weight of unsaturated carboxylic acid of 3 to 5 carbon atoms.

4. A liquid lipstick as in claim 3, said copolymer includes 25–35% by weight of $C_1$ to $C_{18}$ N-substituted alkyl acrylamide.

5. A liquid lipstick as in claim 1, wherein said alkyl acrylate/methacrylate component comprises a $C_3$ to $C_8$ alkyl acrylate/methacrylate, said N-substituted alkyl acrylamide component comprises a $C_4$ to $C_{10}$ N-substituted alkyl acrylamide, and said unsaturated carboxylic acid component comprises an acid selected from the group consisting of acrylic acid and methacrylic acid.

6. A lipstick as in claim 1, wherein said acrylate/methacrylate component comprises at least one material selected from the group consisting of isobutyl methacrylate, butyl acrylate, and methyl methacrylate.

7. A lipstick as in claim 1, wherein said N-substituted acrylamide component comprises at least one material selected from the group consisting of t-octylacrylamide and t-butylacrylamide.

8. A lipstick as in claim 1, wherein said N-substituted acrylamide component comprises t-octylacrylamide.

9. A liquid lipstick as in claim 1, further comprising silica.

10. A liquid lipstick as in claim 1, wherein said cellulose material comprises hydroxypropylcellulose.

11. A lipstick as in claim 1, wherein said lipstick comprises approximately 0.5 to approximately 10 weight percent of said copolymer and approximately 0.1 to approximately 5.0 weight percent hydroxypropylcellulose.

12. A lipstick as in claim 11, further comprising:

0.1 to 5 weight percent methyl glucose ether;

0.1 to 20 weight percent isostearyl alcohol;

0.1 to 10 weight percent silica;

up to 10 weight percent fragrance; and up to 10 weight percent botanical extracts.

13. A lipstick as in claim 12, comprising 0.5 to 4.5 weight percent methyl glucose ether, 2 to 4 weight percent isostearyl alcohol, and 1 to 2 weight percent silica.

14. A liquid composition for coloring skin comprising:

an copolymer consisting essentially of 10–75% by weight acrylate/methacrylate, 10–70% by weight N-substituted acrylamide and 5–40% by weight unsaturated carboxylic acid;

a thickener material;

alcohol; and colorant.

15. A liquid composition as in claim 14, wherein said thickener material comprises hydroxypropylcellulose.

16. A liquid composition as in claim 14, wherein said alcohol comprises isostearyl alcohol and isopropyl alcohol.

17. A liquid composition as in claim 14, wherein said alcohol consists essentially of isostearyl alcohol, isopropyl alcohol, and ethanol.

18. A liquid composition as in claim 14, further comprising shellac.

19. A liquid composition as in claim 14, further comprising an alcohol desensitizer component to inhibit the stinging of skin due to said alcohol.

20. A liquid composition for coloring skin comprising effective amounts of:

an acrylates/octylacrylamide copolymer component consisting essentially of an acrylate/methacrylate, an octylacrylamide and an unsaturated carboxylic acid;

a thickener component;

alcohol; and colorant.

* * * * *